United States Patent [19]

Klein et al.

[11] 4,264,331
[45] Apr. 28, 1981

[54] CHARGED NON-CONDUCTIVE POLAR GAS SENSING ELEMENT AND DETECTION SYSTEM

[75] Inventors: Carl F. Klein, Milwaukee; Paul E. Thoma, Burlington; John E. Aukofer, Milwaukee, all of Wis.

[73] Assignee: Johnson Controls, Inc., Milwaukee, Wis.

[21] Appl. No.: 950,413

[22] Filed: Oct. 11, 1978

Related U.S. Application Data

[63] Continuation-in-part of Ser. No. 821,515, Aug. 3, 1977, abandoned.

[51] Int. Cl.³ .................. G01N 27/62; G11C 13/02
[52] U.S. Cl. ............................ 23/232 E; 307/400; 324/61 R; 338/34; 340/628; 340/632; 361/313; 422/98
[58] Field of Search .............. 23/232 E; 422/98, 54; 73/23.1, 232, 25-27, 29, 73, 74; 324/61 R; 338/34 R; 340/628, 630, 632; 361/312, 313; 179/111 E; 307/88 ET

[56] References Cited

U.S. PATENT DOCUMENTS

| | | | |
|---|---|---|---|
| 3,189,802 | 6/1965 | Zisman | 324/32 X |
| 3,612,778 | 10/1971 | Murphy | 307/88 E X |
| 3,754,219 | 8/1973 | Klein | 340/237 R |
| 3,875,433 | 4/1975 | Uchikawa | 179/111 E X |
| 3,989,463 | 8/1975 | Klein et al. | 361/280 |
| 4,037,310 | 7/1977 | Van Turnhout | 307/88 ET X |

Primary Examiner—Michael S. Marcus
Attorney, Agent, or Firm—Andrus, Sceales, Starke & Sawall

[57] ABSTRACT

An air pollutant and/or fire combustion sensing apparatus includes a charged insulating sensing electrode layer establishing an electric field as the result of electric dipoles and/or electric monopoles in or on the sensing layer. The layer has a high surface and bulk resistivity. The layer has a minimal water absorption at environmental humidities. The electric field of the sensing layer creates electrostatic sensing reactions with the gaseous products of combustion and environmental pollution and produces an amplification of the charge detection characteristic to alter the charge of the electrode. In a capacitive sensor, the sensing layer is mounted within and in spaced relation to a ground shield member. The sensing layer is thereby exposed and produces a sensitive capacitive detector for sensing of a wide spectrum of combustion products and the like. Optimum results are obtained by the charging of dielectric materials such as polytetrafluoroethylene (Teflon TFE), perfluoroalkoxy (Teflon PFA), fluorinated ethylene-propylene (Teflon FEP), polystyrene or polyethylene, which also provide detection as the result of their gaseous adsorption characteristics. A high input impedance detecting circuit with good electrometer characteristics responds to the change in the charge, particularly on the surface.

12 Claims, 4 Drawing Figures

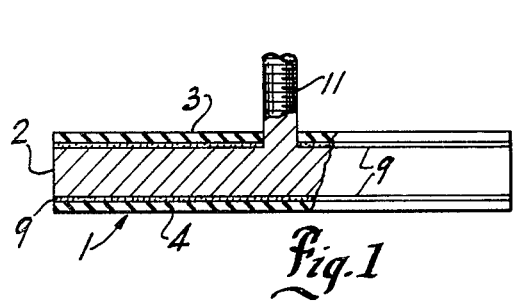
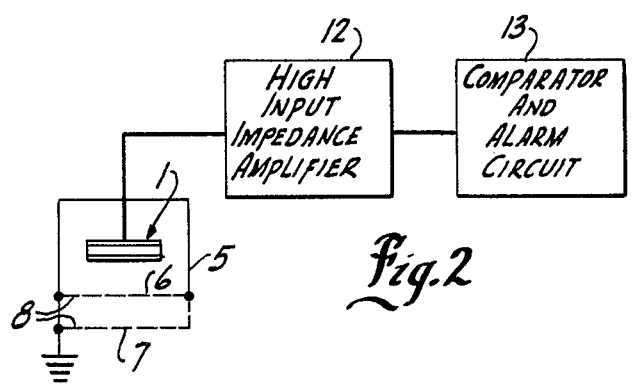
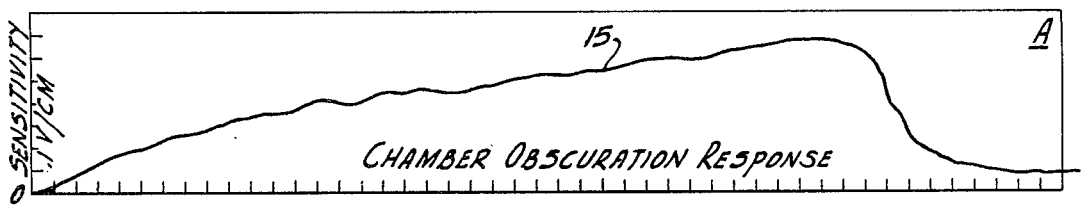
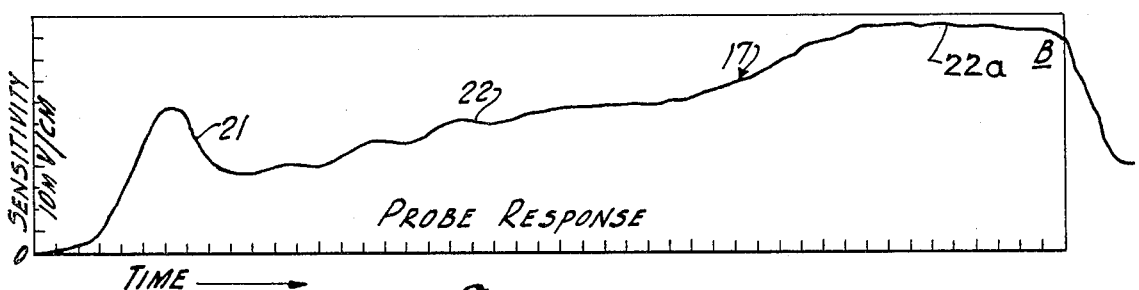
Fig. 3
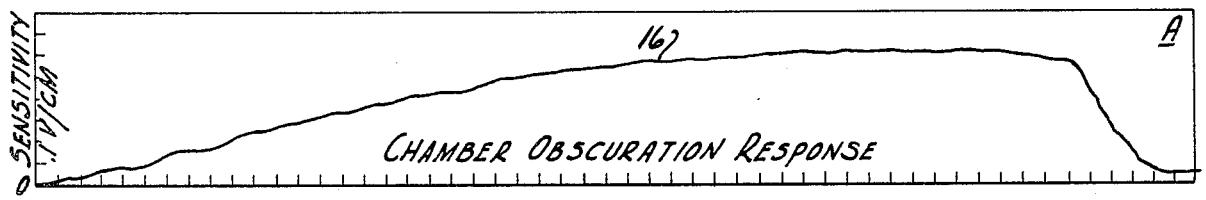
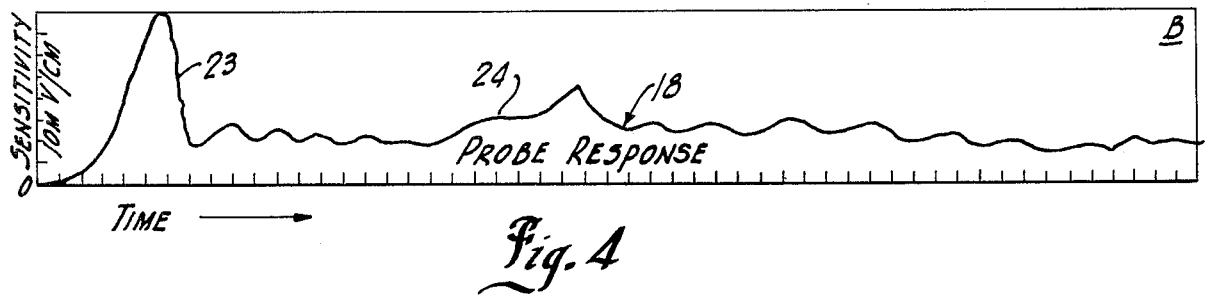
Fig. 4

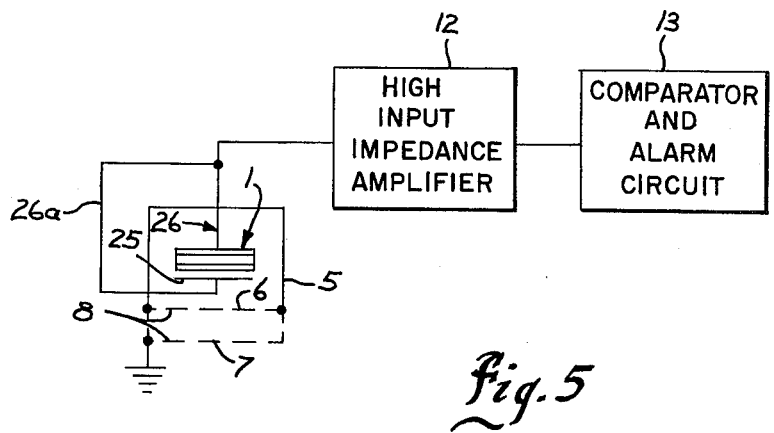
Fig. 5
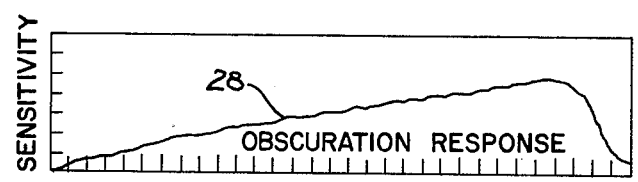
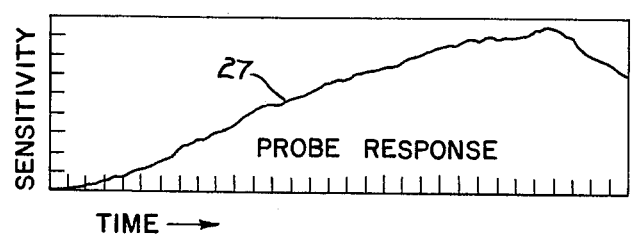
Fig. 6

CHARGED NON-CONDUCTIVE POLAR GAS SENSING ELEMENT AND DETECTION SYSTEM

BACKGROUND OF THE INVENTION

This is a continuation-in-part of application, Ser. No. 821,515, of Carl F. Klein et al, filed Aug. 3, 1977 for "Charged Non-Conductive Polar Gas Sensing Element and Detection System" and now abandoned.

This invention relates to a gaseous product detection system and particularly to an improved sensing element for detecting environmental borne constituents generated as a result of combustion, pollution or the like.

Combustion detection and alarm systems employing various sensing and detecting means have been suggested, such as thermal, flame, photo-electric, ionization chamber, semi-conductors of a metal oxide or polymeric organic material, and electrolyte cell sensors. The various prior art devices are discussed in the present inventors' copending application, Ser. No. 702,918, entitled "Non-Conductive Polar Gas Sensing Element and Detection System", filed on July 6, 1976 and assigned to the same assignee as this application, wherein a sensing element includes a sensitive non-conductive surface which has a surface resistivity in excess of $1 \times 10^{10}$ ohms per square and a bulk resistivity in excess of $1 \times 10^{12}$ ohms-cm and which is essentially free of dipole-hydrogen bonding forces. Preferably, the surface resistivity exceeds $1 \times 10^{15}$ ohms/square and its bulk resistivity exceeds $1 \times 10^{15}$ ohm-cm at 50% R. H. (relative humidity). The output is preferably detected using a high impedance output amplifier such as disclosed in U.S. Pat. No. 3,754,219.

The minimizing of the component of surface energy due to hydrogen bonding appears as a principal factor responsible for the usefulness of the material in that invention and generally should have a value of less than 5.0 ergs/cm$^2$ and preferably less than 1 erg/cm$^2$. Materials disclosed therein as particularly useful include polytetrafluoroethylene (TFE), perfluoroalkoxy (PFA), fluorinated ethylene-propylene (FEP), which are available under the Teflon trademark of E. I. du Pont de Nemours and Company, polystyrene, and polyethylene, (all of which have a dipole-hydrogen bonding value of less than 1 erg/cm$^2$). The materials adsorb polar gas molecules generated by combustion, with a resulting induced charge which can be detected. The probe or electrode is also sensitive to ion radicals and charged particles associated with products of combustion and the like which move in close proximity to the surface.

SUMMARY OF THE PRESENT INVENTION

The present invention is directed to a pollutant sensitive non-conductive material and generally includes the use of a non-conductive material which has been specially charged to develop a charge enhancing field. More particularly, in accordance with the present invention, the detection material employed as the exposed sensing surface of a probe means is an electret which contains either electric dipoles and/or electric monopoles. The enhancing field can thus result from aligned dipoles or from a charge deposited on the surface or preferably into the material. Materials which can be specially processed and are particularly useful are disclosed in the previously identified application and particularly include polytetrafluoroethylene (Teflon TFE), perfluoroalkoxy resin (Teflon PFA), fluorinated ethylene propylene copolymer (FEP), polystyrene and polyethylene although other materials can also be used. The high volume and surface resistivity of such materials are important to hold the charge for an extended period of time.

Such materials also have a low water absorption and adsorption characteristic. The non-conductive materials can be charged in any suitable manner. Aligned dipoles are formed employing a thermoelectric procedure. Dipoles may also be aligned by stressing or stretching of appropriate ferroelectric materials. Charge injection may be created by placing the material in an electric field and producing suitable charges using a corona discharge, an electron beam or the like. Charging can also be performed by liquid and triboelectric charging techniques.

The charged non-conductive or dielectric layer's response to combustion products includes an initial pulse followed by a unique increasing ramp response function. The ramp response function is not noted in a non-charge, non-conductive adsorption sensing layer. The electrostatic or field effect associated with the unique charged layer would, of course, explain this difference in response and the improved response to combustion and other similar environmental borne products.

More particularly, a charged sensing probe in a particularly satisfactory embodiment includes a conductive base plate having a mounting and connecting stud on the back side. The charged non-conductive layer is intimately attached to the base plate in any suitable manner. The probe is mounted within a suitable outer conductor which acts as ground shield and forms a capacitive type sensing unit, with the non-conductive layer spaced from the shield, thus exposing its surface to the environment. Thus, in the broadest aspect of this invention, the outer conductor may be significantly spaced from the probe such that the probe means acts as an adsorption sensing device. In another embodiment, the ground shield is located in close spacement to the probe, or an additional plate electrode is so located, and a capacitor sensor is formed, with the high intensity electric field to the ground shield providing a capacitive response.

Although the charged non-conductive sensor creates a more sensitive probe than has been created in the prior art, the magnitude of the signal is generally such that a high input impedance device which also has good electrometer characteristics should be employed to detect the signal. A suitable output signal detector is shown in U.S. Pat. Nos. 3,754,219 and 3,989,463. However, significantly less amplification is required to develop a useful output signal.

The present invention has been found to provide a significantly greater sensitivity to particulate and gaseous mediums resulting from combustion and like environmentally borne products.

BRIEF DESCRIPTION OF THE DRAWING

The drawing furnished herewith illustrates a preferred construction of the present invention in which the above advantages and features are clearly disclosed as well as others which will be clear from the following description of such embodiments.

In the drawing:

FIG. 1 is an elevational view of a sensing probe having a charged dielectric layer in accordance with the present invention;

FIG. 2 is a block circuit diagram of a fire detection apparatus incorporating a sensing probe of the present invention;

FIG. 3 is a graphical illustration showing the sensitivity of the charged dielectric material to gaseous molecules;

FIG. 4 is a view similar to FIG. 2 for a non-charged dielectric material.

FIG. 5 is a view of the probe head assembly providing a unique capacitor sensor; and FIG. 6 is a view similar to FIGS. 3 or 4 and illustrating the response of the sensor shown.

DESCRIPTION OF THE ILLUSTRATED EMBODIMENTS

Referring to the drawing and, in particular to FIGS. 1–2, a sensing probe 1 constructed in accordance with the teaching of the present invention is shown including a supporting metal plate 2 and novel sensitive surfaces 3 and 4 on the opposite faces thereof. The surface may, of course, be applied to only one side. The probe 1 may be employed directly but is preferably mounted in a particularly satisfactory embodiment, within an outer supporting housing or case 5 having a pair of grounded cup-shaped perforated plates or electrodes 6 and 7 to form a free space between the probe 1 and the shields. If the sheild is spaced close to the probe a capacitance sensor is created as more fully developed hereinafter. An arrangement employing a metal probe is shown in the previously identified application of the present inventors. Perforations 8 in both of the shielding electrodes 6 and 7 permit essentially free access of the surrounding environment into the interior of the electrodes and into contact with the special probe or electrode.

In accordance with the illustrated embodiment of FIG. 1, the probe is a disc-like element including the base metal plate 2 formed of a conducting material and with a special non-conductive and reactive material 3-4, suitably secured, in intimate contact with the opposite faces thereof. The material 3-4 may be deposited as a coating or a film-like material may be secured to the plate 2 by a suitable adhesive 9 such as FEP or PFA Teflon or a silicone contact adhesive. Other means may of course by employed. For example, a conductive coat may be vacuum deposited on the reactive material and then mechanically attached to the base plate 2. A supporting post or stud 11 is secured to the plate 2, suitably supports the probe 1 and forms a circuit connection means for connecting of the probe into the circuit. The probe 1 is connected as the input of high impedance detection and processing circuit 12 as shown in FIG. 2, and operates a suitable alarm circuit 13 of any suitable construction.

Generally, the probe 1 functions to generate an electrical signal in the presence of gaseous products such as encountered in the incipient and following stages of combustion. By use of an appropriate circuit such signal can be detected. The electronic processing circuit 12, may of course, be of any suitable construction adapted to provide a high impedance input connection to the probe 1 such as generally disclosed in the inventor's previously identified disclosure and in their U.S. Pat. no. 3,989,463 which issued Nov. 2, 1972 to Carl F. Klein et al as well as U.S. Pat. No. 3,754,219. No further illustration or description is therefore given of elements 12 and 13.

Each of the probe coatings or layers 3-4 is a non-conductive material which has been charged to develop an electric field at the surface which produces a significant and special and unique response to the products of combustion including those created during the incipient and initial stages. Layers 3 and 4 may be of the same or different materials.

Combustion sensitive layer 3, and layer 4, is a non-conductive material which is treated so as to contain either electric dipoles and/or electric monopoles and is thus an electret which is defined as a charged insulating material which produces a permanent electric field. This field can result either from aligned dipoles, or because of extra charge deposited in or on the electret. Such a material is the electrostatic analogy of a permanent magnet except that a dielectric material may contain both electric dipoles and electric monopoles. This fundamental difference explains why a dielectric may be polarized in many more ways than a magnetic material.

The holding of an electric charge is of prime importance to the present invention, since the life of the electret is a function of its charge holding ability. A principal property of the electret material that is responsible for this charge holding ability is its electrical resistivity. Generally, the material must have a high volume and surface resistivity to hold the charge for an extended period of time. In general, the volume resistivity should be greater than $1 \times 10^{12}$ ohm cm at 50% RH and the surface resistivity should be greater than $1 \times 10^{10}$ ohms/square at 50% RH. The preferred volume and surface resistivities are greater than $1 \times 10^{15}$ ohm cm and $1 \times 10^{15}$ ohms/square respectively.

In practical applications, the sensor materials should also have a low water adsorption at environmental relative humidities up to 90% RH, and preferably is less than 1% at 95% RH. The above water absorption values are on a weight basis after 24 hours of exposure.

Another desirable characteristic of the electret material is a surface energy component due primarily to dispersion bonding forces with a minimum contribution from dipole-hydrogen bonding forces. In other words, the exposed electret surface has a minimum of polar functional groups on its surface. Typical materials that have these characteristics are the same used in the previously identified copending application of the inventors and include polytetrafluoroethylene (Teflon TFE), polystyrene, and polyethylene.

As disclosed in the above application, materials with values of $\gamma^h_s$ less than 5.0 ergs/cm$^2$ are the most useful as the electret material of this invention.

Other useful electret materials would include fluorinated ethylene propylene copolymer (FEP), perfluoroalkoxy resin (Teflon PFA), Ionomer resin, and polypropylene. Any other non-conductor, which can be charged and retains such charge, may, of course, be used.

The dielectric material is preferably such as that disclosed in the previously identified copending application such that the unique electret-adsorption sensing mechanism is created. As the sensing mechanism's dual name implies, its sensing reaction is two-fold in nature. The dielectric material thus performs as an adsorber of combustion products as in the copending application, but also is capable of and functions with an electrostatic sensing reaction. The electret sensing phenomena thus differs from the simple adsorption reactions in that its detection capability is further dependent on coulombic electrostatic forces.

The electric field associated with the electret material amplifies the adsorption and charge detection phenomena associated with non-charged dielectric materials. The electret's amplification of its non-charged adsorption capability would appear to be explained by the action of the electric field associated with the electret tending to align the adsorbed polar gas molecules, thus increasing the effect of their induced field. The electric field also has the ability to attract charged aerosols, ion radicals, and polar gas molecules. The degree of attraction associated with any such polar gas molecules which are present in the free space is of course dependent upon the degree the coulomb forces are able to overcome the thermal energy associated with the polar gases.

The addition of the electret sensing phenomena to that associated with the dielectric adsorption probe material results in the generation of the noticeably different product sensing probe signature. This difference in combustion signatures to a smoldering cotton wick in a UL smoke chamber is shown in FIG. 3 and 4 by probe responses for a charged probe and non-charged probe.

FIGS. 3 and 4 each includes a series of two graphical illustrations, in which curves A includes similar traces 15 and 16 of the obscuration response with time of an Underwriters Laboratories (UL) smoke chamber employed in testing each sample and resulting from insertion of a smoldering cotton wick into the chamber. Curves B are a pair of traces 17 and 18 of the response or signal characteristic of the probe. The traces for the charged dielectric or electret probe includes an initial pulse 21 followed by a distinct ramp function signal. The ramp signal 22 is shown reaching a consistent level 22a. This resulted from the saturation of the amplifier and would have otherwise continued to increase. In contrast, the non-charged probe includes an initial pulse 23 followed by an essentially constant and substantially reduced output signal portion 24. The charged dielectric with the adsorption enhancement field thus produces a distinctly different sensitivity characteristic, with the field maintaining a continous response. The electret or charged dielectric provides detection of a wide spectrum of products generated by combustion and air pollution, including the various toxic and noxious polar gases and charged particles. The electret sensing probe with the continuous sensitivity thus is capable of sensing the fire in both the incipient smoldering and the flaming stages of combustion.

The amplified adsorption of the polar gases on the surface of the sensing element increases the magnitude of the charge induced in the electret's sensing surface. In order to sense this charge, a high input impedance circuit with good electrometer characteristics is generally required. However, the gain of this amplifier is noticeably lower than that required by a non-electret adsorption sensor. As a result the complexity and therefore the cost of the electret's sensing circuitry is considerably reduced. Generally, the output signal detection units disclosed in the previously identied patents can be satisfactorily employed with the present invention.

A wide variety of methods are available for forming electrets. The classical thermoelectric method employs a strong electric field applied to an insulator while it is heated and subsequently cooled. The dipole alignment that occurs at high temperature is frozen in once the material cools. This method relies on the temperature dependence of dipole rotation under an external applied field. A method without heat uses charge injection in which an electric field is applied to the dielectric material with external charges accelerated toward and imbedded in the dielectric material. The charges may be produced by ionization of the air caused by the high electric field (corona discharge charging). Alternatively, charges may also be produced by an electron beam and carefully controlled in energy and density as the beam is scanned over the surface of the dielectric material.

Liquid and triboelectric charging techniques are also useful. In liquid charging, intimate electrical contact to the electret surface is achieved by using a liquid film. A voltage is applied across the electret using the liquid as one electrode which is in contact with the exposed electret material and a second metal conductor, such as aluminum which is usually vapor deposited on the opposite surface of the electret material, as the counterelectrode. The liquid contact is then withdrawn while maintaining the external voltage. The developed charge remains on in the dielectric to form an electret, the magnitude of which corresponds to the applied voltage. Triboelectric or contact electrification results from friction between two surfaces with relative motion. Even the careful removal of a conductor in contact with a dielectric usually produces a characteristic charge separation.

As such methods have been heretofore employed to produce charged dielectric materials, no further description thereof is given.

The stability and life of the surface charged electrets are functions of the material's surface contamination and resistivity and the life is also affected by the presence of atmospheric ions which are attracted to the electret's surface by coulombic forces. Such electrets thus require effective methods of shielding from the ions in their surroundings such as preferably provided by the illustrated ground shield members. The charge injected electrets are readily formed with lifetimes of several hundred years with proper shielding and thus may be employed where long unattended life is required.

In order to sense changes in the charge of the sensor layer the detection circuitry generally should include a high input impedance with good electrometer characteristics. A variety of circuit designs are available for obtaining extremely high input impedance. The four approaches most widely used are field effect transistors (FET's) an electrometer tube, a vibrating capacitor, or a varactor bridge. The inventors have found that the field effect transistor is a particularly satisfactory circuit for the input impedance device and may for example be similar to the detection system shown in the previously identified U.S. patents. Operating as a voltage amplifier an impedance greater than $10^{10}$ ohms and preferably greater than $10^{12}$ ohms is obtained with low offset currents, good voltage and current stability, comparable noise performance, and low power dissipation.

The present invention thus teaches that a highly significant result is obtained by the use of a charged dielectric material wherein the signal changes are enhanced as a result of the interaction between the pollutant products and the field created by the charged material.

Although shown with the surface material attached to the opposite faces of a plate-like element, other configurations can, of course, be employed. For example, a single side of the support plate may be coated and other than plate-like support members may be readily employed.

As previously noted, shield element 6 maybe located in close spacement to the probe unit 1 to form a capacitor sensor for sensing of fire generated products and like environmental borne products. In addition, the capacitor sensor maybe uniquely formed as shown in FIG. 5, which illustrates a modification to the assembly as shown in FIG. 2. Corresponding elements of the embodiments of FIGS. 2 and 5 are correspondingly numbered for simplicity and clarity of explanation.

More particularly, referring to FIG. 5, the sensing head unit is modified to include capacitor plate 25 which is located in close spacement to the probe unit 1, and particularly the sensing surface 4. The illustrated capacitor plate 25 includes a connecting post or stud 26 which may also be employed to suitably support the plate in place. As illustrated in full the capacitor may be connected to the plate post 26 which is the input stud of the probe 1 and thus connected to the high imput impedance amplifier 12 by the lead 26a. Alternatively, the plate 25, can be connected to the ground or any other reference potential. Further, the embodiment of the invention as shown in FIG. 5, is a parallel plate capacitor although any other capacitive geometry could be employed which defines a free space between the electret sensing surface 4 and the capacitor plate 25. The embodiment of the invention as illustrated in FIG. 5 produces an additional detection mechanism to that of the non-compacitive type probe sensing system. Thus, as previously noted, the electret sensing material provides for a dual response mechanism including the first response mechanism based upon the adsorption characteristic of the surface material and the second response mechanism based upon the alignment and attractment of charged, gaseous products developing a multiple or build-up layer of charge of polar gas molecules on the surface. In addition, the capacitor geometry creates a high intensity field which interacts with the particulate matter in the smoke as well as with non-charged gas molecules with the induction of an induced dipole moment in the particulate matter and the gas molecules. Thus, the high intensity electric field tends to separate the negative and positive charge within the molecule and within the particulate. Thus, by locating the sensor plate elements close to each other and thereby forming a capacitor sensor the electric field intensity is increased to a level to provide effective and operable induced polarization of the particulate matter. For example, the electret can be readily charged to a typical operating level of 3,000 volts per square inch and the second plate located from the probe on the order of one-eighth of an inch, thereby significantly increasing the field and creating the induced dipole movement in the particulate matter and gas molecules. Although charging of a sensor as described above to any significant level can be expected to produce some improvement in response, the inventors have generally found that the sensing capacitors electric field strength should be on the order of $3.150 \times 10^5$ volts/m to obtain practically significant results.

Thus, smoke as it enters the electric field becomes polarized, with positive induced charges equal in magnitude to negative induced charges. In this process, electrons in the smoke are displaced from equilibrium positions, forming induced dipoles of polarization, $P=Nqd$. The induced smoke charge will always appear in such a way that the field of the electret set up by it ($E_s$) opposes the electric field ($E_o$) of the capacitor. The resultant capacitor field E is the sum of $E_o$ and $E_s$ and has the same polarity as $E_o$ except for the fact that it is smaller due to the induced smoke polarization which tends to weaken the capacitor's original external field. The weakening of the capacitor's electric field reveals itself as a reduction in potential difference between the capacitor's plates. Here, $V=Ed$, where $V=$voltage, $E=$electric field strength and $d=$distance. As shown in FIG. 6, the response of the capacitor sensor is a continuously increasing ramp. The induced dipole movements in the gas molecules and particles, thus tend to smooth the characteristic of the curve 27 and eliminate the drop in the output after the initial smoke charge 28 (FIG. 6) is detected.

The induced polarization of a molecule in the smoke cloud can also be described with reference to its structure. If no external field is present, the molecule is in its normal electrical configuration. In the capacitor's electric field, the electron cloud shifts from its normal electrical configuration to a more deformed polar configuration. The shift is such that the force on the electron cloud by the electric field of the charged plates and the force on the electron cloud due to the coulombic attraction between the charges are balanced, and stable equilibrium exists.

where $$F_E = F_C \qquad \text{(Eq. 1)}$$

$$F_E = NqE \qquad \text{(Eq. 2)}$$

and $$F_C = \frac{(Nq)^2 d}{4\pi\epsilon_o R^3} \qquad \text{(Eq. 3)}$$

Therefore, $$NqE = \frac{(Nq)^2 d}{4\pi\epsilon_o R^3} \qquad \text{(Eq. 4)}$$

$$4\pi\epsilon_o R^3 E = Nqd \qquad \text{(Eq. 5)}$$

The dipole moment of the molecule can therefore be written:

$$P = Nqd = 4\pi\epsilon_o R^3 E = \alpha E \qquad \text{(Eq. 6)}$$

where $$\alpha = 4\pi\epsilon_o R^3 \qquad \text{(Eq. 7)}$$

is the molecule's electronic polarizability. The polarizability $\alpha$ can be seen to depend not on the number of charges N of the molecule but rather on its radius R. One is therefore able to control the size of the particles being detected by controlling the magnitude of the electric field. The dipole moment can be seen to be proportional to the strength of the capacitor's electric field.

The phenomena may also be described, including the induced polarization mechanism, in terms of changes in a capacitor's relative permittivity. The passage of smoke forms a dielectric between the plates of a charged capacitor and will produce a change in the capacitor's relative permittivity. This change in permittivity will result in a change in the electric field intensity between the plates of the capacitor and thus, a change in the voltage across it. If no dielectric smoke is present, Gauss Law states:

$$Q_c = Q_o = \epsilon_o \int E \cdot ds = \epsilon_o E_o A \quad \text{(Eq. 10)}$$

$$E_c = E_o = \frac{Q}{\epsilon_o A} \quad \text{(Eq. 11)}$$

If the dielectric smoke is present, $$Q_c = Q_o - Q_i = \epsilon_o \int E \cdot ds = \epsilon_o E_c A \quad \text{(Eq. 12)}$$

$$E_c = \frac{Q_o}{\epsilon_o A} - \frac{Q_i}{\epsilon_o A} \quad \text{(Eq. 13)}$$

$$\frac{Q_o}{A} = \epsilon_o E_c + \frac{Q_i}{A} \quad \text{(Eq. 14)}$$

$$D = \epsilon_o E_c + P_i \quad \text{(Eq. 15)}$$

$$D = \frac{Q_o}{A}$$

is the electric flux density
$E = V/d$ is the electric field intensity $$P_i = \frac{Q_i}{A}$$

is the induced polarization
However, since $$D = \epsilon_o \epsilon_r E \quad \text{(Eq. 16)}$$

we can write $$D = \epsilon_o \epsilon_r E = \epsilon_o E + P_i \quad \text{(Eq. 17)}$$

$$P_i = \epsilon_o (\epsilon_r - 1) E \quad \text{(Eq. 18)}$$

or $$\epsilon_r = 1 + \frac{P}{\epsilon_o E} \quad \text{(Eq. 19)}$$

Since smoke detection is accomplished using induced polarization in a capacitor's electric field, the detector's particulate and liquid droplet sensitivity is proportional to the charge on the capacitor.

$$S \sigma Q_c = Q_o - Q_1 = DA = \epsilon_o \epsilon_r EA = \epsilon_o \epsilon_r \frac{VA}{d} \quad \text{(Eq. 20)}$$

Where
S = smoke sensitivity
D = the capacitor's electric flux density
A = capacitor's area
$\epsilon_o$ = permittivity of dielectric
$\epsilon_r$ = relative permittivity of dielectric
E = the capacitor's electric field intensity
V = the capacitor's voltage
d = the spacing distance of the capacitor plates.

The important aspect of this invention is the exposure of the gaseous products to a significant surface area of the uniquely charged dielectric material in combination with a means to detect a change in its charge. In relatively large areas, a plurality of units may be distributed throughout the area and connected to a signal processing circuit or to individual processing circuits. The present invention thus further enhances the use of a non-conductive sensor while maintaining a relatively low cost unit having a long, reliable life. The invention can be employed in any smoke or pollution environment in which the products generated interact with the special charged surface means to produce a change in the surface charge.

Various modes of carrying out the invention are contemplated as being within the scope of the following claims particularly pointing out and distinctly claiming the subject matter which is regarded as the invention.

We claim:

1. A method of detecting gaseous contaminants in a gaseous sample comprising precharging a dielectric material with a fixed charge, said dielectric material forming an exposed surface of a sensing probe, contacting a gaseous sample suspected of containing gaseous contaminants with said precharged dielectric material by passing said gaseous sample through a space defined by a surface of said precharged dielectric material and a shield member which is held at a fixed reference voltage to form a reference electrode, reacting said gaseous contaminants with said dielectric material, promoting said reaction between said dielectric material and said gaseous sample by a charge enhanced electric field formed by said precharged dielectric material, generating an electric output signal from said reaction, amplifying said output signal by passing said signal through a high impedance amplifying means, and passing said amplified signal to a detecting means for indicating the presence of said gaseous contaminants.

2. The method of claim 1 wherein said precharging of said dielectric material creates aligned dipoles in said dielectric to form said electric charge.

3. The method of claim 1 wherein said precharging creates surface charges on said exposed surface of said dielectric material for establishing said electric field at the sensing surface.

4. The method of claims 1 or 3 wherein said precharging creates entrapped electric charges in said dielectric material for further establishing said electric field at the sensing surface.

5. The method of claim 1 wherein said dielectric material has a volume resistivity greater than $1 \times 10^{12}$ ohm-cm at 50% RH, a surface resistivity greater than $1 \times 10^{10}$ ohms/square at 50% RH and a water absorption capability of less than 1% by weight at 95% environmental RH.

6. The method of claim 1 wherein said dielectric material is selected having a surface energy component due primarily to dispersion bonding forces with a minimum contribution from dipole-hydrogen bonding forces.

7. The method of claim 1 wherein said dielectric material is selected from the group consisting of polytetrafluoroethylene (TFE), perfluoroalkoxy (PFA), fluorinated ethylene propylene (FEP), polystyrene, polyethylene, polypropylene and ionomer resins.

8. The method of claim 1 wherein said material includes a predominate portion selected from polytetrafluorethylene (TFE), perfluoroalkoxy (PFA), fluorinated ethylene propylene (FEP), polystyrene, polyethylene, polypropylene and ionomer resins.

9. The method of claim 1 including intimately attaching said dielectric material to a plate-like base conductor member, and forming said shield member as an outer perforated enclosure with said sensing probe mounted within the enclosure.

10. The method of claim 1 including mounting said sensing probe in close spaced relation to said shield member to create a sensing capacitor.

11. The method of claim 1 wherein the shield member is connected to ground.

12. The method of claim 1 including said precharging establishes a field strength between said sensing probe and said shield member of at least $3.150 \times 10^5$ volts/m.

* * * * *